(12) United States Patent
Leser-Reiff et al.

(10) Patent No.: US 6,784,173 B2
(45) Date of Patent: Aug. 31, 2004

(54) AROMATIC DICARBOXYLIC ACID DERIVATIVES

(75) Inventors: Ulrike Leser-Reiff, Penzberg (DE); Tim Sattelkau, Mannheim (DE); Gerd Zimmermann, Linkenheim (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 177 days.

(21) Appl. No.: 10/167,677

(22) Filed: Jun. 11, 2002

(65) Prior Publication Data

US 2003/0013757 A1 Jan. 16, 2003

(30) Foreign Application Priority Data

Jun. 15, 2001 (EP) ............................................. 01114496

(51) Int. Cl.$^7$ .................... C07D 333/38; C07D 409/12; C07D 213/40; C07D 317/58; A61K 31/00
(52) U.S. Cl. ........................ 514/231.5; 549/72; 549/60; 544/379; 544/146; 544/295; 544/121; 544/364; 546/212; 546/280.4; 546/19; 548/527; 548/315.1; 514/448; 514/444; 514/252.13; 514/422; 514/326; 514/336; 514/397; 514/278; 514/252.14; 514/235.8; 514/253.1
(58) Field of Search ...................... 549/72, 60; 514/448, 514/444, 252.13, 422, 326, 336, 231.5, 397, 278, 252.14, 235.8, 253.1; 544/379, 146, 295, 121, 364; 546/212, 280.4, 19; 548/527, 315.1

(56) References Cited

U.S. PATENT DOCUMENTS 4,279,836 A 7/1981 Nishikido et al.

5,369,108 A 11/1994 Breslow et al.

FOREIGN PATENT DOCUMENTS

| EP | 0 847 992 | 7/1998 |
| WO | WO 95/31977 | 11/1995 |
| WO | WO 98/55449 | 12/1998 |
| WO | WO 01/38322 | 5/2001 |

OTHER PUBLICATIONS

Ranadive, V. B. et al., Indian Journal of Chemistry Section B: Organic Incl. Medicinal Publications & Informations Directorate, New Delhi, In. vol. 12 No. 33 B, Dec. 1994 pp. 1175–1177.

Khan, Mohammed, J. Chem. Soc. Perkin Trans. vol. 2 (1988) (2) pp. 213–219.

Kobashi, Kyoichi et al., Biochim. Biophys. Acta (1971) vol. 227 (2) pp. 429–441.

*Primary Examiner*—Richard L. Raymond
*Assistant Examiner*—Hong Liu
(74) *Attorney, Agent, or Firm*—George W. Johnston; Patricia S. Rocha-Tramaloni

(57) ABSTRACT

Compounds of formula I

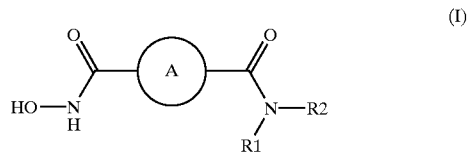

wherein A, $R^1$ and $R^2$ are defined in the specification. These compounds are useful as HDAC inhibitors. Also disclosed are methods of making and using said compounds.

27 Claims, No Drawings

AROMATIC DICARBOXYLIC ACID DERIVATIVES

The invention relates to aromatic dicarboxylic acid derivatives, or pharmaceutically-acceptable salts thereof, which possess anti-cell-proliferation activity such as antitumor activity and are accordingly useful in methods of treatment of humans and other animals. The invention also relates to processes for the manufacture of said dicarboxylic acid derivatives, to pharmaceutical compositions containing the derivatives and to their use in the treatment of cell-proliferation disorders.

BACKGROUND OF THE INVENTION

Transcriptional regulation is a major event in cell differentiation, proliferation, and apoptosis. Transcriptional activation of a set of genes determines cell destination and for this reason transcription is tightly regulated by a variety of factors. One of its regulatory mechanisms involved in the process is an alteration in the tertiary structure of DNA, which affects transcription by modulating the accessibility of transcription factors to their target DNA segments. Nucleosomal integrity is regulated by the acetylation status of the core histones. In a hypoacetylated state, nucleosomes are tightly compacted and thus are nonpermissive for transcription. On the other hand, nucleosomes are relaxed by acetylation of the core histones, with the result being permissiveness to transcription. The acetylation status of the histones is governed by the balance of the activities of histone acetyl transferase (HAT) and histone deacetylase (HDAC). Recently, HDAC inhibitors have been found to arrest growth and apoptosis in several types of cancer cells, including colon cancer, T-cell lymphoma, and erythroleukemic cells. Given that apoptosis is a crucial factor for cancer progression, HDAC inhibitors are promising reagents for cancer therapy as effective inducers of apoptosis (Koyama, Y., et al., Blood 96 (2000) 1490–1495).

Several structural classes of HDAC inhibitors have been identified and are reviewed in Marks, P. M., et al., J. Natl. Cancer Inst. 92 (2000) 1210–1216. More specifically, WO 98/55449 and U.S. Pat. No. 5,369,108 report alkanoyl hydroxamates with HDAC inhibitory activity.

It has now been found that certain aromatic dicarboxylic acid derivatives are more potent inhibitors of cell-proliferation than the compounds reported in the aforementioned references. Furthermore, these compounds have HDAC inhibitiory activity.

DESCRIPTION OF THE INVENTION

The invention is directed to an aromatic dicarboxylic acid derivative of the formula I

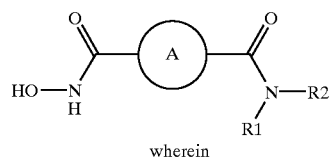

(I)

wherein

denotes a phenyl ring which may be unsubstituted or substituted by 1, 2 or 3 substituents independently selected from a halogen atom, an (1–4C)alkyl-, trifluoromethyl-, hydroxy-, (1–4C)alkoxy-, nitro-, amino-, (1–4C)alkylamino-, di[(1–4C)alkyl]-amino-, (1–4C)alkanoylamino, a (1–3C) alkylenedioxy-group or an acyl group, or alternatively,

denotes a thiophene ring which may be unsubstituted or substituted by 1 or 2 substituents independently selected from a halogen atom, an (1–4C)alkyl-, trifluoromethyl-, hydroxy-, (1–4C)alkoxy-, nitro-, amino-, (1–4C)alkylamino-, di[(1–4C)alkyl]-amino- or a (1–4C) alkanoylamino, a (1–3C)alkylenedioxy-group or an acyl group, and R1 and R2 are each independently selected from
a hydrogen atom;
a branched or unbranched (1–14C)alkyl group, which may be unsubstituted or substituted with 1 or several substituents independently selected from the group consisting of a halogen-, hydroxy-, nitro-, amino-, carbocyclic- or a heterocyclic group,
and wherein at a chain length of larger than 2 C-atoms one or several non adjacent C-atoms may be replaced by a corresponding number of heteroatoms such as oxygen, nitrogen or sulfur,
and wherein 2 C-atoms may be bound together by a double or triple bond;
a carbocyclic group;
or a heterocyclic group;
or alternatively, R1 and R2 together with the nitrogen atom to which they are attached form a 3–6 membered ring that may contain additional heteroatoms independently selected from nitrogen, oxygen and sulfur, said ring optionally being annulated to a carbocyclic ring or a heterocyclic ring, said —NR$^1$R$^2$ ring being unsubstituted or optionally substituted by 1, 2, or 3 substituents independently selected from a halogen atom, an (1–4C)alkyl-, trifluoromethyl-, hydroxy-, (1–4C) alkoxy-, aryl-, hetaryl-, arylalkyl, arylalkyloxy-, aryloxy, (1–3C)alkylenedioxy-, nitro-, amino-, (1–4C) alkylamino-, di[(1–4C)alkyl]amino-, (1–4C) alkanoylamino- or an acyl-group.

An alkyl group may be e.g. pentyl, hexyl or 3-methyl-butyl.

A substituted alkyl group may be e.g. benzyl, phenethyl, tetrahydro-furan-2-yl-methyl or 2-cyclohex-1-enyl-ethyl.

An alkyl group where one or several non adjacent atom groups may be replaced by oxygen, nitrogen or sulfur atoms may be e.g. 3-isopropoxy-propyl or 2-methylsulfanyl-ethyl.

An alkyl group wherein 2 atoms may be bound together by a double or triple bond may be e.g. 1-hexinyl or 2-heptenyl.

"Annulated" as used herein means the fusion of a new ring to a molecule via two new bonds.

A carbocyclic group may be a non-aromatic ring system having 3–7 carbon ring atoms, for example cyclopentane, cyclohexane, cyclohexene or cyclopropane, said ring system being unsubstituted or optionally substituted by 1, 2, or 3 substituents independently selected from a halogen, (1–4C) alkyl-, trifluoromethyl-, hydroxy-, (1–4C)alkoxy-, aryl-, hetaryl-, arylalkyl, arylalkyloxy-, aryloxy, (1–3C) alkylenedioxy-, nitro-, amino-, (1–4C)alkylamino-, di[(1–4C)alkyl]amino-, (1–4)alkanoylamino- or an acyl-group. Said ring atoms optionally may be annulated to an aryl or hetaryl group, to form e.g. an indane or a tetraline. A carbocyclic group as herein defined also may be an aryl group.

An aryl group is a carbocyclic conjugated ring system, for example phenyl, naphthyl, preferably phenyl, which may be unsubstituted or substituted by 1, 2, or 3 substituents independently selected from a halogen atom, an (1–4C)alkyl-, trifluoromethyl-, hydroxy-, (1–4C)alkoxy-, arylalkyloxy-, aryloxy, (1–3C)alkylenedioxy-, nitro-, amino-, (1–4C) alkylamino-, di[(1–4C)alkyl]amino-, (1–4C) alkanoylamino-, carboxyl-, carboxyalkyl- or an acyl-group.

A heterocyclic group may be a non-aromatic ring system having 3–7 ring members, said ring members comprising carbon atoms and one or two hetero atoms independently chosen from nitrogen, oxygen, and sulfur. Examples of heterocyclic groups include piperidino, morpholino, pyrrolidino and piperazino. Said ring system may be unsubstituted or substituted by 1, 2, or 3 substituents independently selected from halogen, (1–4C)alkyl-, trifluoromethyl-, hydroxy-, (1–4C)alkoxy-, aryl-, hetaryl-, arylalkyl, arylalkyloxy-, aryloxy, (1–3C)alkylenedioxy-, nitro-, amino-, (1–4C)alkylamino-, di[(1–4C)alkyl]amino-, (1–4C) alkanoylamino, or an acyl-group. Moreover, said ring members optionally may be annulated to an aryl or hetaryl group, to form e.g. a tetrahydrochinoline, tetrahydroisochinoline or a dihydroindole. A heterocyclic group as defined herein also may be a hetaryl group.

A hetaryl group is either a 5 or 6 membered cyclic conjugated ring system with one or two hetero atoms independently chosen from nitrogen, oxygen, and sulfur, for example pyridinyl, thiophenyl, furyl or pyrrolyl, or an annulated bicyclic conjugated ring system like indolyl-, quinolyl- or isoquinolyl-, which may be unsubstituted or substituted by 1, 2, or 3 substituents independently selected from a halogen atom, an (1–4C)alkyl-, trifluoromethyl-, hydroxy-, (1–4C)alkoxy-, arylalkyloxy-, aryloxy, (1–3C) alkylenedioxy-, nitro-, amino-, (1–4C)alkylamino-, di[(1–4C)alkyl]amino-, (1–4C)alkanoylamino, or an acyl group.

When R1 and R2 together with the nitrogen atom form a 3–6 membered ring which may contain additional heteroatoms independently selected from nitrogen, oxygen and sulfur, it may be e.g. piperidine, piperazine or morpholine.

A suitable value for a substituent when it is a halogen atom is, for example, fluoro, chloro, bromo and iodo; when it is (1–4C)alkyl is, for example, methyl, ethyl, propyl, isopropyl, butyl, isobutyl, sec-butyl; when it is (1–4C) alkoxy is, for example, methoxy, ethoxy, propoxy, isopropoxy or butoxy; when it is (1–4C)alkylamino is, for example, methylamino, ethylamino or propylamino; when it is di-[(1–4C)alkyl]amino is, for example, dimethylamino, N-ethyl-N-methylamino, diethylamino, N-methyl-N-propylamino or dipropylamino; when it is (1–4C) alkanoylamino is, for example, formylamido, acetamido, propionamido or butyramido; when it is (1–3C) alkylenedioxy is, for example, methylenedioxy, ethylenedioxy or propylenedioxy; and when it is acyl is, for example, formyl, acetyl, propionyl, benzoyl, or phenylacetyl.

In a preferred embodiment, R1 is hydrogen and R2 has one of the above values. In a more preferred embodiment, R2 is a (1–14C)alkyl group. Most preferrably, R2 is an arylalkyl—radical, for example the benzyl—radical or substituted benzyl—radicals.

Preferred are compounds wherein A denotes a thiophene ring. Even more preferred are compounds wherein the thiophene ring is unsubstituted. Most preferred are compounds wherein two carboxylic moieties are bonded at positions 2 and 5 of a further unsubstituted thiophene ring. Enantiomers, diastereoisomers, racemates and mixtures thereof and pharmaceutically acceptable salts of aromatic dicarboxylic acid derivatives of the formula I are also part of the invention.

The invention is also directed to a pharmaceutical composition comprising a therapeutically effective amount of an aromatic dicarboxylic acid derivative of the formula I, or a pharmaceutically-acceptable salt thereof, as defined above, in association with a pharmaceutically-acceptable diluent or carrier. The pharmaceutical composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository. In general the above compositions may be prepared in a manner using conventional excipients. The aromatic dicarboxylic acid derivative will normally be administered to a warm-blooded animal at a unit dose within the range 5–5000 mg per square meter body area of the animal, i.e. approximately 0.1–100 mg/kg, and this normally provides a therapeutically-effective dose. A unit dose form such as a tablet or capsule will usually contain, for example 1–250 mg of active ingredient. Preferably a daily dose in the range of 1–100 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided an aromatic dicarboxylic acid derivative of the formula I as defined hereinbefore for use in a method of treatment of the human or animal body by therapy. It has now been found that the compounds of the present invention possess anti-cell-proliferation properties due to inhibition of histone deacetylase. Accordingly the compounds of the present invention provide a method for treating the proliferation of malignant cells. These compounds are useful in the treatment of cancer by providing an anti-proliferative effect, particularly in the treatment of cancers of the breast, lung, colon, rectum, stomach, prostate, bladder, pancreas and ovary. It is in addition expected that a derivative of the present invention will possess activity against a range of leukemias, lymphoid malignancies and solid tumors such as carcinomas and sarcomas in tissues such as the liver, kidney, prostate and pancreas.

Thus according to this aspect of the invention there is provided the use of an aromatic dicarboxylic acid derivative of the formula I, or a pharmaceutically-acceptable salt thereof, as defined herein in the manufacture of a medicament for use in the production of an anti-cell-proliferation effect in a warm-blooded animal such as a human being.

According to a further feature of this aspect of the invention there is provided a method for producing an anti-cell-proliferation effect in a warm-blooded animal, such as man, in need of such treatment which comprises administering to said animal an effective amount of an aromatic dicarboxylic acid derivative as defined hereinbefore.

The anti-cell-proliferation treatment defined hereinbefore may be applied as a sole therapy or may involve, in addition to the aromatic dicarboxylic acid derivative of the invention, one or more other anti-tumor substances, for example those selected from, for example, mitotic inhibitors, for example vinblastine; alkylating agents, for example cis-platin, carboplatin and cyclophosphamide; inhibitors of microtubule assembly, like paclitaxel or other taxanes; antimetabolites, for example 5-fluorouracil, capecitabine, cytosine arabinoside and hydroxyurea, or, for example, intercalating antibiotics, for example adriamycin and bleomycin; immunostimulants, for example trastuzumab; DNA synthesis inhibitors, e.g. gemcitabine; enzymes, for example asparaginase; topoisomerase inhibitors, for example etoposide; biological response modifiers, for example interferon; and anti-hormones, for example antioestrogens such as tamoxifen or, for example antiandrogens such as (4'-cyano-3-(4-fluorophenylsulphonyl)-2-hydroxy-2-methyl-3'-(trifluoromethyl)-propionanilide, or other therapeutic agents and principles as described in, for example, Cancer: Principles & Practice of Oncology, Vincent T. DeVita, Jr., Samuel Hellmann, Steven A. Rosenberg; 5th Ed., Lippincott-Raven Publishers 1997. Such conjoint treatment may be achieved by way of the simultaneous, sequential or separate dosing of individual components of the treatment. According to this aspect of the invention there is provided a pharmaceutical product comprising an aromatic dicarboxylic acid derivative of the formula I as defined hereinbefore and an additional anti-tumor substance as defined hereinbefore for the conjoint treatment of cancer.

Another object of the present invention is a pharmaceutical composition containing a therapeutically effective amount of one or more compounds of the invention in admixture with pharmaceutically acceptable excipients and/or diluents.

Examples for physiologically acceptable salts of compounds of formula I are salts with physiologically acceptable bases. These salts can be, among others, alkali, earth alkali, ammonium and alkylammonium salts, for example sodium, potassium, calcium, tetra-methyl-ammonium salts.

The compounds of formula I may exist in a racemic mixture. The separation of racemic compounds into their enantiomers can be performed by chromatography on an analytical, semipreparative or preparative scale using suitable optically active stationary phases with suitable eluents. Suitable optically active stationary phases include, but are not limited to, silica (e.g. ChiraSper,Merck; Chiralpak OT/OP, Baker), cellulose esters or carbamates (e.g. Chiracel OB/OY, Baker) or others (e.g. Crownpak, Daicel or Chiracel OJ-R, Baker). Other methods for the separation of enantiomers can also be applied, like the formation of diastereomeric compounds from compounds of the formula I together with other optically active compounds, e.g. camphorsulfonic acid or brucin, and separation of these diastereomeric compounds, followed by the liberation from the optically active agent. Enantiomerically enriched or pure compounds of formula I are also obtainable by the usage of optically active starting materials.

Preparation of the Compounds of the Invention

An aromatic dicarboxylic acid derivative of the formula I, or a pharmaceutically-acceptable salt thereof, may be prepared by any process known to be applicable to the preparation of chemically-related compounds. Such processes, when used to prepare an aromatic dicarboxylic acid derivative of the formula I, or a pharmaceutically-acceptable salt thereof, are provided as a further feature of the invention and are illustrated by the following representative examples in which, unless otherwise stated, A, R1 and R2 have any of the meanings defined above. Necessary starting materials may be obtained by standard procedures of organic chemistry. The preparation of such starting materials is described within the accompanying non-limiting examples. Alternatively necessary starting materials are obtainable by analogous procedures to those illustrated which are within the ordinary skill of an organic chemist.

(a) One preferred method for the production of compounds of the formula I involves the reaction of compounds of the formula II

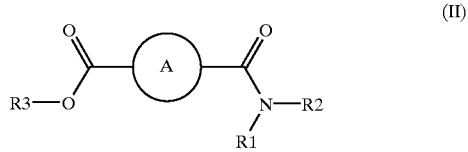

(II)

wherein A, R1 and R2 have the meaning defined above and R3 is a (1–4C)alkyl group, preferably a methyl or ethyl group, with hydroxylamine in the presence of a suitable base. The reaction is carried out in an inert solvent or diluent such as methanol or ethanol at temperatures between 0° C. and 100° C., conveniently at or near ambient temperature, and at a pH between 10 and 12. A suitable base is, for example, an alcoholate, for example, sodium methylate.

Compounds of formula II are prepared from compounds of the formula III wherein A and R3 have the meaning defined hereinbefore

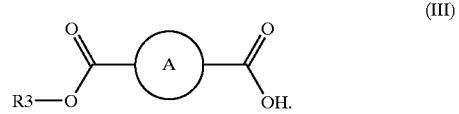

(III)

This reaction typically involves a two-step one-pot procedure. In the first step, the carboxylate of the formula III becomes activated. This reaction is carried out in an inert solvent or diluent, for example, in dichloromethane, dioxane, or tetrahydrofuran, in the presence of an activating agent. A suitable reactive derivative of an acid is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol; an active ester formed by the reaction of the acid and N-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide, or the product of the reaction of the acid and bis-(2-oxo-3-oxazolidinyl)-phosphorylchloride. The reaction is carried out between −30° C. and 60° C., conveniently at or below 0° C. In the second step, an amine of the formula HNR1R2 in which R1 and R2 have the meaning defined hereinbefore is added to the solution, at the temperature used for the activation, and the temperature is slowly adjusted to ambient temperature. An appropriate scavenger base like e.g. triethylamine, or diisopropyethlyamine may be added to the reaction mixture. These methods are well known to those skilled in the art. In principle, all methods for the synthesis of amides as used in peptide chemistry as described in e.g. "Methoden der organischen Chemie (Houben-Weyl)" Vol. XV/1 and XV/2 are also applicable.

There are quite a few compounds of formula III described in the literature. For example, the prototypic terephthalic monomethylester is described in e.g. Z. Phys. Chem.

(Leipzig) 262 (3) (1981) 445–448. It is also commercially available. Thiophene-2,5-dicarboxylic acid monomethyl ester is described in e.g. U.S. Pat. No. 2,680,731. These monoesters are usually prepared by selective saponification of the diester, but other method may be useful as well and are well known to those skilled in the art.

(b) Another preferred method for the preparation of compounds of the formula I is the deprotection of compounds of the formula IV

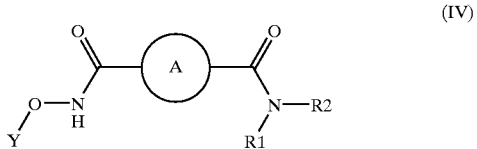

wherein Y is a suitable protecting group and A, R1 and R2 have the meaning defined hereinbefore.

Compounds of the formula IV are new and included within the scope of the present invention.

Suitable protecting groups may be the benzyl-, p-methoxybenzyl-, tert.butyloxycarbonyl-, trityl-, or silyl groups such as the trimethylsilyl- or dimethyl-tert.butylsilyl-group. The reactions carried out depend on the type of the protecting group. When the protecting group is a benzyl- or p-methoxybenzyl group, the reaction carried out is a hydrogenolysis in an inert solvent such as an alcohol like methanol or ethanol, in the presence of a noble metal catalyst such as palladium on a suitable carrier such as carbon, barium sulfate, or barium carbonate, at ambient temperature and pressure. When the protecting group is the tert.butyloxycarbonyl-, trityl-, or a silyl group such as the trimethylsilyl- or dimethyl-tert.butylsilyl-group, the reaction is carried out in the presence of acids at a temperature between −20° C. and 60° C., preferably between 0° C. and ambient temperature. The acid may be a solution of hydrochloric acid in an inert solvent such as diethyl ether or dioxane, or trifluoro acetic acid in dichloromethane. When the protecting group is a silyl group such as the trimethylsilyl or dimethyl-tert.butylsilyl group, the reaction can also be carried out in the presence of a fluoride source such as sodium fluoride or tetrabutyl ammonium fluoride in an inert solvent such as dichloromethane. Not necessarily all protecting groups Y are compatible with all groups R1 or R2. In cases where the features of these groups do not allow the usage of a certain protecting group, other protecting groups Y or other methods of preparation need to be applied.

Compounds of formula IV are obtained from the reaction of compounds of formula V

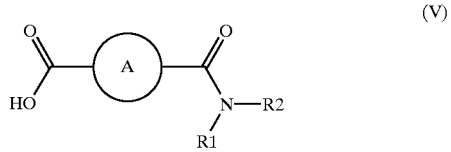

with a compound of the formula VI

wherein Y is a suitable protecting group as described above. This reaction typically involves a two-step one-pot procedure. In the first step, the carboxylate of the formula V becomes activated. This reaction is carried out in an inert solvent or diluent, for example, in dichloromethane, dioxane, or tetrahydrofuran, in the presence of an activating agent. A suitable reactive derivative of an acid is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol; an active ester formed by the reaction of the acid and N-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide, or the product of the reaction of the acid and bis-(2-oxo-3-oxazolidinyl)-phosphorylchloride. The reaction is carried out between −30° C. and 60° C., conveniently at or below 0° C. In the second step, compound VI is added to the solution, at the temperature used for the activation, and the temperature is slowly adjusted to ambient temperature. These methods are well known to those skilled in the art. In principle, all methods for the synthesis of amides as used in peptide chemistry as described in e.g. "Methoden der organischen Chemie (Houben-Weyl)" Vol. XV/1 and XV/2 are also applicable.

Compounds of the formula V are prepared from compounds of the formula II by hydrolysis. The conditions under which the hydrolysis is carried out depend on the nature of the group R3. When R3 is a methyl or ethyl group, the reaction is carried out in the presence of a base, for example, lithium hydroxide, sodium hydroxide, or potassium hydroxide in an inert solvent or diluent, for example, in methanol or ethanol. When R3 is the tert.butyl group, the reaction is carried out in the presence of an acid, for example, a solution of hydrochloric acid in an inert solvent such as diethyl ether or dioxane, or trifluoroacetic acid in dichloromethane. When R3 is the benzyl group, the reaction is carried out by hydrogenolysis in the presence of a noble metal catalyst such as palladium or platinum on a suitable carrier, such as carbon. Not necessarily all methods of hydrolysis are compatible with all groups R1 or R2. In cases where the features of these groups do not allow the usage of a certain method of hydrolysis, other methods of preparation need to be applied.

(c) Another preferred method for the preparation of compounds of the formula I is the reaction of a compound of the formula V with hydroxylamine. This reaction typically involves a two-step one-pot procedure. In the first step, the carboxylate of the formula V becomes activated. This reaction is carried out in an inert solvent or diluent, for example, in dichloromethane, dioxane, or tetrahydrofuran, in the presence of an activating agent. A suitable reactive derivative of an acid is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol; an active ester formed by the reaction of the acid and N-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide, or the product of the reaction of the acid and bis-(2-oxo-3-oxazolidinyl)-phosphorylchloride. The reaction is carried out between −30° C. and 60° C., conveniently at or below 0° C. In the second step, hydroxylamine is added to the solution, at the temperature used for the activation, and the temperature is slowly adjusted to ambient temperature. These methods are well known to those skilled in the art. In principle, all methods for the synthesis of amides as used in peptide chemistry as described in e.g. "Methoden der organischen Chemie (Houben-Weyl)" Vol. XV/1 and XV/2 are also applicable.

(d) Compounds of formula I can also be prepared with methods of solid phase supported synthesis. Terephthalic acid or 2,5-thiophenedicarboxylic acid is reacted with a hydroxylamine moiety (—O—$NH_2$) bound to a resin, e.g. a Wang resin (Wang-O—$NH_2$ resin was supplied by EMC microcollections, Tutbingen) to form a resin-bound hydroxamic acid. The second carbonic acid moiety is reacted with an amine by standard methods of amide formation as described in e.g. "Methoden der organischen Chemie (Houben-Weyl)" Vol. XV/1 and XV/2. After this, the hydroxamic acid is liberated from the solid support. This can be done for example with TFA. The crude product can be purified by LC-MS, if necessary.

The invention will now be illustrated in the following non-limiting examples in which, unless otherwise stated:
  (i) evaporations were carried out by rotary evaporation in vacuo and work-up procedures were carried out after removal of residual solids such as drying agents by filtration;
  (ii) operations were carried out at ambient temperature, that is in the range 18–25° C. and under an atmosphere of an inert gas such as argon or nitrogen;
  (iii) column chromatography (by the flash procedure) and high pressure liquid chromatography (HPLC) were performed on Merck Kieselgel silica or Merck Lichroprep RP-18 reversed-phase silica obtained from E. Merck, Darmstadt, Germany,
  (iv) yields are given for illustration only and are not necessarily the maximum attainable;
  (v) melting points were determined using a Mettler SP62 automatic melting point apparatus, an oil-bath apparatus or a Kofler hot plate apparatus.
  (vi) the structures of the end-products of the formula I were confirmed by nuclear (generally proton) magnetic resonance (NMR) and mass spectral techniques (Micromass Platform II machine using APCI or Micromass Platform ZMD using electrospray);
  (vii) intermediates were not generally fully characterized and purity was assessed by thin layer chromatography;
  (viii) the examples were actually performed; and
  (viv) the following abbreviations have been used:
DMF, N,N-dimethylformamide;
DMSO, dimethylsulphoxide;
THF, tetrahydrofuran;
MeOH, methanol;
HCl, hydrochloric acid;
NaH, sodium hydride
$CH_2Cl_2$, dichloromethane;
$H_2SO_4$, sulphuric acid
sat., saturated
sol., solution
rt, room temperature
eq, equivalent

EXAMPLE 1

Thiophene-2,5-dicarboxylic acid 2-hydroxyamide 5-[(naphthalen-1-ylmethyl)-amide] (1a)

1.9 g Thiophene-2,5-dicarboxylic acid monomethyl ester and 1.2 mL N-methylmorpholine is dissolved in 20 mL of $CH_2Cl_2$ at −10° C. To this solution is added 1.5 mL isobutyl chloroformate. After 10 min of stirring, 1.7 mL 1-(aminomethyl)-naphthalene in 5 mL of $CH_2Cl_2$ is added. The cooling bath is removed and the reaction mixture is allowed to reach rt. After 90 min, 10 mL of water and 10 mL 2N HCl are added. The phases are separated, and the organic phase is washed with water. After evaporation of the solvent there is obtained 4.4 g crude 5-[(naphtalen-1-ylmethyl)-carbamoyl]-thiophene-2-carboxylic acid methyl ester (1b) which is purified by recrystalisation from ethylacetate, petrol ether, yielding 58%, mp 125° C.

To a solution of 550 mg hydroxylamine hydrochloride in 8 mL MeOH is added ⅔ of a solution of 275 mg of sodium in 8 mL of MeOH. To this, a solution of 1.30 g 5-[(naphtalen-1-ylmethyl)-carbamoyl]-thiophene-2-carboxylic acid methyl ester (1b) in 30 mL MeOH is added, followed by the remaining sodium methylate solution. After stirring for 4 h at rt the solvent is evaporated. 20 mL of water are added, acidified with 4 mL 50% acetic acid, and the precipitate is collected by filtration. After trituration with THF there is obtained 0.76 g thiophene-2,5-dicarboxylic acid 2-hydroxyamide 5-[(naphthalen-1-ylmethyl)-amide] (1a) as a white powder, mp 170° C.

EXAMPLE 2

Thiophene-2,5-dicarboxylic acid 2-hydroxyamide 5-(4-trifluoromethyl-benzylamide) (2a)

2a is prepared from thiophene-2,5-dicarboxylic acid monomethyl ester in an analogous manner to that described for the preparation of 1a example 1. The last step yields 40% of thiophene-2,5-dicarboxylic acid 2-hydroxyamide 5-(4-trifluoromethyl-benzylamide) (2a), mp. 172–174° C.

EXAMPLE 3

N-hydroxy-N'-naphthalen-1-ylmethyl-terephthalamide (3a)

1 eq of Wang-O—$NH_2$ is shaken with 11 eq of terephthalic acid, 5.5 eq N,N'-diisopropylcarbodiimide, 5.5 eq 1-hydroxybenzotriazole and 25 eq diisopropylethylamine in DMF for 4 h at 25° C. After that, the resin is washed with DMF (5 times), MeOH (3 times), THF (3 times), $CH_2Cl_2$ (3 times) and diethylether (3 times). The resin is then shaken with 5 eq pentafluorophenyl trifluoroacetate and 10 eq pyridine. After that, the resin is washed with DMF (2 times), followed by $CH_2Cl_2$ (2 times), followed by diethylether (2 times). The resin is then shaken with 5 eq of naphtalenemethylamine, 10 eq of diisopropylethylamine and leq of 1-hydroxybenzotriazole. It is then shaken with 5 eq pentafluorophenyl trifluoroacetate and 10 eq pyridine. After that, the resin is washed with DMF (2 times), followed by $CH_2Cl_2$ (2 times). To liberate the product from the solid support, the resin is shaken with 50% TFA in dry $CH_2Cl_2$ with 5% triisopropylsilane added at rt for 1 h. The liquid phase is filtered, the resin washed with $CH_2Cl_2$ (3 times), and the combined filtrates are evaporated. The crude product is dissolved in tert-butanol/$H_2O$ (80:20) and freeze-dried. To neutralize any remaining TFA, 100 μL of a 25% NH₄OH-sol is added and freeze-dried, again. The remaining solid is purified by preparative LC-MS to N-hydroxy-N'-naphthalen-1-ylmethyl-terephthalamide, MS (APCI): 321.1 (M+1)

EXAMPLE 4

Thiophene-2,5-dicarboxylic acid 2-(3-chloro-benzylamide) 5-hydroxyamide (4a)

9.0 g Thiophene-2,5-dicarboxylic acid monomethyl ester is refluxed in 30 mL of thionylchloride until gas evolution has ceased. The mixture is evaporated and the residue is slowly added to a solution of 10.3 g 3-chlorobenzylamine and 20 g triethylamine in 180 mL CH₂Cl₂ at 0° C. After 15 min the cooling bath is removed and the reaction mixture is allowed to reach rt. After 2 h it is quenched with water, the phases are separated, and the aqueous phase is extracted with CH₂Cl₂. The combined organic phases are dried with Na₂SO₄ and evaporated yielding a crude product. This is purified by recrystallisation from diethylether/heptane yielding 13.9 g (93%) crude 5-[(3-chlorobenzyl)-carbamoyl]-thiophene-2-carboxylic acid methyl ester (4b), mp 91–93° C. To a solution of 2.9 g hydroxylamine hydrochloride in 45 mL MeOH is added 25 mL of a solution of 1.4 g sodium in 40 mL of MeOH. To this, a solution of 6.4 g ester 4b in 30 mL MeOH is added, followed by the remaining 15 mL of the sodium methylate solution. After stirring for 3 h at rt the solution is acidified with 1N HCl and some ethylacetate is added. Thiophene-2,5-dicarboxylic acid 2-(3-chloro-benzylamide) 5-hydroxyamide (4a) precipitates as a white solid; 4.7 g, 73%, mp. 183° C.

EXAMPLE 5

Thiophene-2,5-dicarboxylic acid 2-(3,5-dimethyl-benzylamide) 5-hydroxyamide (5a)

5a is prepared from thiophene-2,5-dicarboxylic acid monomethyl ester in an analogous manner to that described for the preparation of 4a example 4. MS (APCI): 305.3 (M+1)

EXAMPLE 6

Thiophene-2,5-dicarboxylic acid 2-hexylamide 5-hydroxyamide (6a)

6a is prepared from thiophene-2,5-dicarboxylic acid monomethyl ester in an analogous manner to that described for the preparation of 4a example 4, mp 171–173° C.

EXAMPLE 7

Thiophene-2,4-dicarboxylic acid 2-(3,5-dimethyl-benzylamide) 4-hydroxyamide (7a)

0.5 g 2-carboxy-thiophen-4-carboxylic acid ethyl ester (M. Janda, J. Srogl, M. Nemec, I. Stibor; Org. Prep. and Proced. Int. 3 (6) (1971) 295.) and 0.67 g N'-(3-dimethylaminopropyl)-N-ethylcarbodiimidxHCl are stirred in 50 mL DCM for 15 min. Then, 0.338 g 3,5-dimethylbenzylamin are added and the mixture is stirred overnight. The solution is extracted with 2N HCl and water, then evaporated. The residue is titurated with isohexan, and the resulting crystals are filtrated and air-dried, yielding 0.58 g (73%) crude 5-(3,5-Dimethyl-benzylcarbamoyl)-thiophene-3-carboxylic acid ethyl ester (7b). This ester in converted to title compound by reaction with hydroxylamine hydrochloride in a manner similar to that described for the conversion of 4b into 4a in example 4. After chromatography (silica, ethylacetate), thiophene-2,4-dicarboxylic acid 2-(3,5-dimethyl-benzylamide) 4-hydroxyamide (7a) is obtained as crystals; 44 mg, 9%, mp: 181° C. (decomp.).

EXAMPLE 8

Thiophene-2,4-dicarboxylic acid 2-(3-chloro-benzylamide) 4-hydroxyamide (8a)

8a is prepared from 2-carboxy-thiophen-4-carboxylic acid ethyl ester in an analogous manner to that described for the preparation of 7a example 7; 163 mg, 34%, mp: 90° C. (decomp.).

EXAMPLE 9

Thiophene-2,4-dicarboxylic acid 4-hydroxyamide 2-(4-trifluoromethyl-benzylamide) (9a)

9a is prepared from 2-carboxy-thiophen-4-carboxylic acid ethyl ester in an analogous manner to that described for the preparation of 7a example 7; 56 mg, 10%, mp: 174–177° C.

EXAMPLE 10

Thiophene-2,4-dicarboxylic acid 2-[(benzo[1,3] dioxol-5-ylmethyl)-amide] 4-hydroxyamide (10a)

10a is prepared from 2-carboxy-thiophen-4-carboxylic acid ethyl ester in an analogous manner to that described for the preparation of 7a example 7; 16 mg, 3%, mp: 182° C. (decomp.).

EXAMPLE 11

Thiophene-2,4-dicarboxylic acid 2-hexylamide 4-hydroxyamide (11a)

11a is prepared from 2-carboxy-thiophen-4-carboxylic acid ethyl ester in an analogous manner to that described for the preparation of 7a example 7; 92 mg, 20%, mp: 150° C. (decomp.).

EXAMPLE 12

Thiophene-2,4-dicarboxylic acid 4-(3,5-dimethyl-benzylamide) 2-hydroxyamide(12a)

5.0 g 2-carboxy-thiophen-4-carboxylic acid ethyl ester (Org. Prep. and Proced. Int. 3 (6) (1971) 295) is dissolved in 50 mL THF and 4.5 g thionylchloride is added. After refluxing for 4 h, the mixture is evaporated. The crude acid chloride is added to a solution of 3.1 g O-benzylhydroxylamine and 3.06 g triethylamine in 80 mL DCM. After stirring for 4 h the solution is washed with 2N HCl and water, dried and evaporated. After titurating the residue with isohexan/diethylether, bright crystals of 5-benzyloxycarbamoyl-thiophene-3-carboxylic acid ethyl ester (12b) are obtained, which are filtered and air-dried; 3.5 g, 46%. 0.46 g NaOH are dissolved in 45 mL ethanol and 5 mL water. The ester 12b is added and the solution refluxed for 2 h. After cooling, the ethanol is evaporated and the aqueous phase extracted with diethylether. The aqueous phase is acidified with 2N HCl and the precipitate formed is collected by filtration, yielding 2.8 g (88%) 5-benzyloxycarbamoyl-thiophene-3-carboxylic acid (12c) as a solid.

0.4 g 5-benzyloxycarbamoyl-thiophene-3-carboxylic acid (12c) is dissolved in 50 mL DCM, and 0.387 g N'-(3- dimethylaminopropyl)-N-ethylcarbodiimid×HCl are added. After stirring for 15 min, 0.195 g 3,5-dimethylbenzylamine is added, and the mixture is stirred overnight.

The solution is extracted with 2N HCl and water, then evaporated. The residue is titurated with ether/isohexan, and the resulting crystals are filtrated and air-dried, yielding 0.44 g (77%) of thiophene-2,4-dicarboxylic acid 2-(benzyloxy-amide) 4-(3,5-dimethyl-benzylamide) (12d). This is hydrogenated in a 1:1 mixture of THF and MeOH using Pd/CaSO$_4$/C and purified by preparative HPLC/MS yielding 12a: MS (APCI): 303.1 (M−1).

EXAMPLE 13

In an analogous manner to that described in the example 12, the following compounds are prepared:
1. Thiophene-2,4-dicarboxylic acid 4-(3-chloro-benzylamide) 2-hydroxyamide
2. Thiophene-2,4-dicarboxylic acid 4-hexylamide 2-hydroxyamide

EXAMPLE 14

4-{[(5-Hydroxycarbamoyl-thiophene-2-carbonyl)-amino]-methyl}-benzoic acid methyl ester In an analogous manner to that described in the example 12, but using 2-carboxy-thiophen-5-carboxylic acid methyl ester and methyl 4-(aminomethyl)-benzoate as starting material, 4-{[(5-Hydroxycarbamoyl-thiophene-2-carbonyl)-amino]-methyl}-benzoic acid methyl ester is prepared, mp.: 156–166° C.

EXAMPLE 15

In an analogous manner to that described in the example 1, and using known methods as described in the literature (e.g. in standard works such as Houben-Weyl, "Methoden der Organischen Chemie, Georg Thieme Verlag", Stuttgart; Organic Reactions, John Wiley & Sons, Inc., New York) the following compounds are prepared and characterized with MS (APCI):

1. 5-(4-benzhydryl-piperazine-1-carbonyl)-thiophene-2-carboxylic acid hydroxyamide
2. thiophene-2,5-dicarboxylic acid 2-benzylamide 5-hydroxyamide
3. thiophene-2,5-dicarboxylic acid 2-hydroxyamide 5-[(3-methyl-butyl)-amide]
4. thiophene-2,5-dicarboxylic acid 2-hydroxyamide 5-(phenethyl-amide)
5. thiophene-2,5-dicarboxylic acid 2-hydroxyamide 5-{[2-(4-methoxy-phenyl)-ethyl]-amide}
6. thiophene-2,5-dicarboxylic acid 2-(4-fluoro-benzylamide) 5-hydroxyamide
7. thiophene-2,5-dicarboxylic acid 2-hydroxyamide 5-[(1,2,3,4-tetrahydro-naphthalen-1-yl)-amide]
8. thiophene-2,5-dicarboxylic acid 2-(2-ethoxy-benzylamide) 5-hydroxyamide
9. thiophene-2,5-dicarboxylic acid 2-(2,4-difluoro-benzylamide) 5-hydroxyamide
10. thiophene-2,5-dicarboxylic acid 2-hydroxyamide 5-indan-1-ylamide
11. thiophene-2,5-dicarboxylic acid 2-[(benzo[1,3]dioxol-5-ylmethyl)-amide] 5-hydroxyamide
12. 5-(4-phenyl-piperazine-1-carbonyl)-thiophene-2-carboxylic acid hydroxyamide
13. thiophene-2,5-dicarboxylic acid 2-hydroxyamide 5-[(3-isopropoxy-propyl)-amide]
14. 5-(4-acetyl-piperazine-1-carbonyl)-thiophene-2-carboxylic acid hydroxyamide
15. thiophene-2,5-dicarboxylic acid 2-dibutylamide 5-hydroxyamide
16. 5-(4-benzyl-piperidine-1-carbonyl)-thiophene-2-carboxylic acid hydroxyamide
17. thiophene-2,5-dicarboxylic acid 2-hydroxyamide 5-[(pyridin-3-ylmethyl)-amide]
18. thiophene-2,5-dicarboxylic acid 2-cyclohexylamide 5-hydroxyamide
19. thiophene-2,5-dicarboxylic acid 2-cyclopropylamide 5-hydroxyamide
20. thiophene-2,5-dicarboxylic acid 2-hydroxyamide 5-{[2-(1-methyl-pyrrolidin-2-yl)-ethyl]-amide}
21. thiophene-2,5-dicarboxylic acid 2-hydroxyamide 5-(2-methoxy-benzylamide)
22. thiophene-2,5-dicarboxylic acid 2-[(2-cyclohex-1-enyl-ethyl)-amide] 5-hydroxyamide
23. thiophene-2,5-dicarboxylic acid 2-hydroxyamide 5-[(2-morpholin-4-yl-ethyl)-amide]
24. thiophene-2,5-dicarboxylic acid 2-hydroxyamide 5-[(2-methylsulfanyl-ethyl)-amide]
25. thiophene-2,5-dicarboxylic acid 2-hydroxyamide 5-[(tetrahydro-furan-2-ylmethyl)-amide]
26. thiophene-2,5-dicarboxylic acid 2-hydroxyamide 5-phenylamide
27. 5-(morpholine-4-carbonyl)-thiophene-2-carboxylic acid hydroxyamide
28. thiophene-2,5-dicarboxylic acid 2-hydroxyamide 5-[(4-methoxy-phenyl)-amide]
29. 5-(pyrrolidine-1-carbonyl)-thiophene-2-carboxylic acid hydroxyamide
30. thiophene-2,5-dicarboxylic acid 2-[(4-benzyloxy-phenyl)-amide] 5-hydroxyamide
31. thiophene-2,5-dicarboxylic acid 2-[(4-chloro-phenyl)-amide] 5-hydroxyamide
32. thiophene-2,5-dicarboxylic acid 2-hydroxyamide 5-[(4-iodo-phenyl)-amide]
33. thiophene-2,5-dicarboxylic acid 2-[(3-ethyl-phenyl)-amide] 5-hydroxyamide
34. thiophene-2,5-dicarboxylic acid 2-[(4-ethyl-phenyl)-amide] 5-hydroxyamide
35. thiophene-2,5-dicarboxylic acid 2-[(3-chloro-phenyl)-amide] 5-hydroxyamide
36. thiophene-2,5-dicarboxylic acid 2-hydroxyamide 5-[(3-iodo-phenyl)-amide]
37. 5-(1,4-dioxa-8-aza-spiro[4.5]decane-8-carbonyl)-thiophene-2-carboxylic acid hydroxyamide
38. thiophene-2,5-dicarboxylic acid 2-hydroxyamide 5-[(3-morpholin-4-yl-propyl)-amide]
39. thiophene-2,5-dicarboxylic acid 2-hydroxyamide 5-pentylamide
40. thiophene-2,5-dicarboxylic acid 2-[(2-diethylamino-ethyl)-amide] 5-hydroxyamide
41. thiophene-2,5-dicarboxylic acid 2-heptylamide 5-hydroxyamide
42. thiophene-2,5-dicarboxylic acid 2-hydroxyamide 5-(isobutyl-amide)
43. thiophene-2,5-dicarboxylic acid 2-hydroxyamide 5-nonylamide
44. thiophene-2,5-dicarboxylic acid 2-hydroxyamide 5-[(1-phenyl-ethyl)-amide]
45. thiophene-2,5-dicarboxylic acid 2-[2-(4-fluoro-phenyl)-ethyl]-amide 5-hydroxyamide
46. thiophene-2,5-dicarboxylic acid 2-hydroxyamide 5-[2-(5-nitro-pyridin-2-ylamino)-ethyl]-amide
47. thiophene-2,5-dicarboxylic acid 2-hydroxyamide 5-(3-methyl-benzylamide)

48. thiophene-2,5-dicarboxylic acid 2-hydroxyamide 5-[(2-p-tolyl-ethyl)-amide]
49. thiophene-2,5-dicarboxylic acid 2-hydroxyamide 5-[3-(2-oxo-pyrrolidin-1-yl)-propyl]-amide
50. thiophene-2,5-dicarboxylic acid 2-hydroxyamide 5-[(2-piperidin-1-yl-ethyl)-amide]
51. thiophene-2,5-dicarboxylic acid 2-cyclobutylamide 5-hydroxyamide
52. thiophene-2,5-dicarboxylic acid 2-(2-fluoro-benzylamide) 5-hydroxyamide
53. thiophene-2,5-dicarboxylic acid 2-hydroxyamide 5-[(2-phenyl-propyl)-amide]
54. thiophene-2,5-dicarboxylic acid 2-(2,3-dimethoxy-benzylamide) 5-hydroxyamide
55. thiophene-2,5-dicarboxylic acid 2-[(1-benzyl-piperidin-4-yl)-amide] 5-hydroxyamide
56. 4-[(5-hydroxycarbamoyl-thiophene-2-carbonyl)-amino]-piperidine-1-carboxylic acid ethyl ester
57. thiophene-2,5-dicarboxylic acid 2-[(3-dimethylamino-2,2-dimethyl-propyl)-amide] 5-hydroxyamide
58. thiophene-2,5-dicarboxylic acid 2-[(3-ethoxy-propyl)-amide] 5-hydroxyamide
59. thiophene-2,5-dicarboxylic acid 2-[(3-dimethylamino-propyl)-amide] 5–58
60. thiophene-2,5-dicarboxylic acid 2-[2-(2-chloro-phenyl)-ethyl]-amide 5-hydroxyamide
61. thiophene-2,5-dicarboxylic acid 2-hydroxyamide 5-(2-trifluoromethyl-benzylamide)
62. thiophene-2,5-dicarboxylic acid 2-hydroxyamide 5-(3-trifluoromethyl-benzylamide)
63. thiophene-2,5-dicarboxylic acid 2-(2,5-difluoro-benzylamide) 5-hydroxyamide
64. thiophene-2,5-dicarboxylic acid 2-(2,6-difluoro-benzylamide) 5-hydroxyamide
65. thiophene-2,5-dicarboxylic acid 2-(3,4-difluoro-benzylamide) 5-hydroxyamide
66. thiophene-2,5-dicarboxylic acid 2-hydroxyamide 5-[(3-imidazol-1-yl-propyl)-amide]
67. thiophene-2,5-dicarboxylic acid 2-[(1-cyclohexyl-ethyl)-amide] 5-hydroxyamide
68. thiophene-2,5-dicarboxylic acid 2-[2-(3-chloro-phenyl)-ethyl]-amide 5-hydroxyamide
69. thiophene-2,5-dicarboxylic acid 2-[2-(3-fluoro-phenyl)-ethyl]-amide 5-hydroxyamide
70. thiophene-2,5-dicarboxylic acid 2-[2-(2,4-dichloro-phenyl)-ethyl]-amide 5-hydroxyamide
71. thiophene-2,5-dicarboxylic acid 2-cyclopropylmethyl-amide 5-hydroxyamide
72. thiophene-2,5-dicarboxylic acid 2-[2-(2-fluoro-phenyl)-ethyl]-amide 5-hydroxyamide
73. thiophene-2,5-dicarboxylic acid 2-[(4-diethylamino-1-methyl-butyl)-amide] 5-hydroxyamide
74. thiophene-2,5-dicarboxylic acid 2-hydroxyamide 5-[(2-pyridin-2-yl-ethyl)-amide]
75. thiophene-2,5-dicarboxylic acid 2-hydroxyamide 5-[(2-pyrrolidin-1-yl-ethyl)-amide]
76. thiophene-2,5-dicarboxylic acid 2-hydroxyamide 5-[(1-methyl-hexyl)-amide]
77. thiophene-2,5-dicarboxylic acid 2-cycloheptylamide 5-hydroxyamide
78. thiophene-2,5-dicarboxylic acid 2-cyclopentylamide 5-hydroxyamide
79. thiophene-2,5-dicarboxylic acid 2-(2,4-dichloro-benzylamide) 5-hydroxyamide
80. thiophene-2,5-dicarboxylic acid 2-[(3-diethylamino-propyl)-amide] 5-hydroxyamide
81. thiophene-2,5-dicarboxylic acid 2-[(1,5-dimethyl-hexyl)-amide] 5-hydroxyamide
82. thiophene-2,5-dicarboxylic acid 2-[(2,2-diphenyl-ethyl)-amide] 5-hydroxyamide
83. 3-[(5-hydroxycarbamoyl-thiophene-2-carbonyl)-amino]-butyric acid ethyl ester
84. thiophene-2,5-dicarboxylic acid 2-[(2-ethyl-hexyl)-amide] 5-hydroxyamide
85. thiophene-2,5-dicarboxylic acid 2-hydroxyamide 5-(4-methoxy-benzylamide)
86. thiophene-2,5-dicarboxylic acid 2-hydroxyamide 5-(4-methyl-benzylamide)
87. thiophene-2,5-dicarboxylic acid 2-hydroxyamide 5-[(3-phenyl-propyl)-amide]
88. thiophene-2,5-dicarboxylic acid 2-[(2-diisopropylamino-ethyl)-amide] 5-hydroxyamide
89. thiophene-2,5-dicarboxylic acid 2-hydroxyamide 5-[2-(4-nitro-phenyl)-ethyl]-amide
90. thiophene-2,5-dicarboxylic acid 2-[(3,3-diphenyl-propyl)-amide] 5-hydroxyamide
91. thiophene-2,5-dicarboxylic acid 2-(2-amino-benzylamide) 5-hydroxyamide
92. Thiophene-2,5-dicarboxylic acid 2-(4-bromo-benzylamide) 5-hydroxyamide
93. Thiophene-2,5-dicarboxylic acid 2-(3,5-bis-trifluoromethyl-benzylamide) 5-hydroxyamide
94. Thiophene-2,5-dicarboxylic acid 2-(3-bromo-benzylamide) 5-hydroxyamide
95. Thiophene-2,5-dicarboxylic acid 2-(3-fluoro-benzylamide) 5-hydroxyamide
96. Thiophene-2,5-dicarboxylic acid 2-hydroxyamide 5-(3-methoxy-benzylamide)
97. Thiophene-2,5-dicarboxylic acid 2-(2-chloro-6-fluoro-benzylamide) 5-hydroxyamide
98. Thiophene-2,5-dicarboxylic acid 2-(4-tert-butyl-benzylamide) 5-hydroxyamide
99. Thiophene-2,5-dicarboxylic acid 2-hydroxyamide 5-{[2-(4-sulfamoyl-phenyl)-ethyl]-amide}
100. Thiophene-2,5-dicarboxylic acid 2-[(2-benzylsulfanyl-ethyl)-amide] 5-hydroxyamide
101. Thiophene-2,5-dicarboxylic acid 2-hydroxyamide 5-{[2-(4-hydroxy-phenyl)-ethyl]-amide}
102. Thiophene-2,5-dicarboxylic acid 2–{[2-(4-chloro-phenyl)-ethyl]-amide}5-hydroxyamide
103. Thiophene-2,5-dicarboxylic acid 2-{[2-(3,4-dimethoxy-phenyl)-ethyl]-amide} 5-hydroxyamide
104. Thiophene-2,5-dicarboxylic acid 2-hydroxyamide 5-[(2-phenoxy-ethyl)-amide]
105. Thiophene-2,5-dicarboxylic acid 2-hydroxyamide 5-[(4-phenyl-butyl)-amide]
106. Thiophene-2,5-dicarboxylic acid 2-[(3,4-dimethyl-phenyl)-amide] 5-hydroxyamide
107. 5-(4-Pyrimidin-2-yl-piperazine-1-carbonyl)-thiophene-2-carboxylic acid hydroxyamide
108. Thiophene-2,5-dicarboxylic acid 2-[(3,4-dimethoxy-phenyl)-amide] 5-hydroxyamide
109. Thiophene-2,5-dicarboxylic acid 2-[(4-tert-butyl-phenyl)-amide] 5-hydroxyamide
110. Thiophene-2,5-dicarboxylic acid 2-hydroxyamide 5-[(4-methoxy-2-methyl-phenyl)-amide]
111. Thiophene-2,5-dicarboxylic acid 2-[(4-dimethylamino-phenyl)-amide] 5-hydroxyamide
112. Thiophene-2,5-dicarboxylic acid 2-hydroxyamide 5-[(4-phenoxy-phenyl)-amide]
113. Thiophene-2,5-dicarboxylic acid 2-hydroxyamide 5-p-tolylamide
114. Thiophene-2,5-dicarboxylic acid 2-hydroxyamide 5-[(4-piperidin-1-yl-phenyl)-amide]
115. 1-(5-Hydroxycarbamoyl-thiophene-2-carbonyl)-piperidine-4-carboxylic acid methyl ester 116. Thiophene-2,5-dicarboxylic acid 2-hydroxyamide 5-[methyl-(1-methyl-piperidin-4-yl)-amide]
117. Thiophene-2,5-dicarboxylic acid 2-hydroxyamide 5-{methyl-[2-(4-nitro-phenyl)-ethyl]-amide}
118. Thiophene-2,5-dicarboxylic acid 2-(butyl-methyl-amide) 5-hydroxyamide
119. Thiophene-2,5-dicarboxylic acid 2-diethylamide 5-hydroxyamide
120. Thiophene-2,5-dicarboxylicacid2-[(4-cyclohexyl-phenyl)-amide] 5-hydroxyamide
121. Thiophene-2,5-dicarboxylic acid 2-hydroxyamide 5-[methyl-(2-methylamino-ethyl)-amide]
122. Thiophene-2,5-dicarboxylic acid 2-[ethyl-(3-ethylamino-propyl)-amide] 5-hydroxyamide
123. 5-[4-(2-Morpholin-4-yl-2-oxo-ethyl)-piperazine-1-carbonyl]-thiophene-2-carboxylic acid hydroxyamide
124. 5-(4-Dimethylcarbamoylmethyl-piperazine-1-carbonyl)-thiophene-2-carboxylic acid hydroxyamide
125. 5-[4-(2-Oxo-2-piperidin-1-yl-ethyl)-piperazine-1-carbonyl]-thiophene-2-carboxylic acid hydroxyamide
126. Thiophene-2,5-dicarboxylic acid 2-hydroxyamide 5-(3-trifluoromethoxy-benzylamide)
127. Thiophene-2,5-dicarboxylic acid 2-hydroxyamide 5-(3-phenoxy-benzylamide)
128. Thiophene-2,5-dicarboxylic acid 2-hydroxyamide 5-[(1-methyl-3-phenyl-propyl)-amide]
129. Thiophene-2,5-dicarboxylic acid 2-hydroxyamide 5-[(3-methoxy-propyl)-amide]
130. Thiophene-2,5-dicarboxylic acid 2-(4-chloro-benzylamide) 5-hydroxyamide
131. Thiophene-2,5-dicarboxylic acid 2-[(2-acetylamino-ethyl)-amide] 5-hydroxyamide
132. Thiophene-2,5-dicarboxylic acid 2-hydroxyamide 5-[(1-methyl-heptyl)-amide]
133. Thiophene-2,5-dicarboxylic acid 2-hydroxyamide 5-[(1-methyl-butyl)-amide]
134. Thiophene-2,5-dicarboxylic acid 2-allylamide 5-hydroxyamide
135. Thiophene-2,5-dicarboxylic acid 2-[(1,3-dimethyl-butyl)-amide] 5-hydroxyamide
136. Thiophene-2,5-dicarboxylic acid 2-hydroxyamide 5-propylamide
137. Thiophene-2,5-dicarboxylic acid 2-sec-butylamide 5-hydroxyamide
138. Thiophene-2,5-dicarboxylic acid 2-butylamide 5-hydroxyamide
139. Thiophene-2,5-dicarboxylic acid 2-(3,4-dichloro-benzylamide) 5-hydroxyamide
140. Thiophene-2,5-dicarboxylic acid 2-(2,3-dichloro-benzylamide) 5-hydroxyamide
141. thiophene-2,5-dicarboxylic acid 2-(2,3-difluoro-benzylamide) 5-hydroxyamide
142. thiophene-2,5-dicarboxylic acid 2-(2-chloro-benzylamide) 5-hydroxyamide
143. thiophene-2,5-dicarboxylic acid 2-(3,4-dimethoxy-benzylamide) 5-hydroxyamide
144. thiophene-2,5-dicarboxylic acid 2-(3,5-difluoro-benzylamide) 5-hydroxyamide
145. thiophene-2,5-dicarboxylic acid 2-[(2-amino-phenyl)-amide] 5-hydroxyamide
146. thiophene-2,5-dicarboxylic acid 2-([4-(2-amino-phenylcarbamoyl)-benzylamide] 5-(benzyloxy-amide)
147. thiophene-2,5-dicarboxylic acid 2-hydroxyamide 5-[methyl-(4-trifluoromethyl-benzyl)-amide]

EXAMPLE 16

In an analogous manner to that described in the example 3, and using known methods as described in the literature (e.g. in standard works such as Houben-Weyl, "Methoden der Organischen Chemie, Georg Thieme Verlag", Stuttgart; Organic Reactions, John Wiley & Sons, Inc., New York) the following compounds are prepared and characterized with MS (APCI):

1. 4-(4-benzhydryl-piperazine-1-carbonyl)-N-hydroxy-benzamide
2. N-hydroxy-N'-pyridin-3-ylmethyl-terephthalamide
3. N-benzyl-N'-hydroxy-terephthalamide
4. N-cyclohexyl-N'-hydroxy-terephthalamide
5. N-cyclopropyl-N'-hydroxy-terephthalamide
6. N-hexyl-N'-hydroxy-terephthalamide
7. N-hydroxy-N'-(3-methyl-butyl)-terephthalamide
8. N-hydroxy-N'-phenethyl-terephthalamide
9. N-hydroxy-N'-[2-(4-methoxy-phenyl)-ethyl]-terephthalamide
10. N-(3-chloro-benzyl)-N'-hydroxy-terephthalamide
11. N-hydroxy-N'-(2-methoxy-benzyl)-terephthalamide
12. N-(4-fluoro-benzyl)-N'-hydroxy-terephthalamide
13. N-hydroxy-N'-(1,2,3,4-tetrahydro-naphthalen-1-yl)-terephthalamide
14. N-hydroxy-N'-(4-trifluoromethyl-benzyl)-terephthalamide
15. N-(2,4-difluoro-benzyl)-N'-hydroxy-terephthalamide
16. N-hydroxy-N'-indan-1-yl-terephthalamide
17. N-benzo[1,3]dioxol-5-ylmethyl-N'-hydroxy-terephthalamide
18. N-hydroxy-4-(4-phenyl-piperazine-1-carbonyl)-benzamide
19. N-(3,5-dimethyl-benzyl)-N'-hydroxy-terephthalamide
20. N-hydroxy-N'-(3-isopropoxy-propyl)-terephthalamide
21. 4-(4-acetyl-piperazine-1-carbonyl)-N-hydroxy-benzamide
22. N,N-dibutyl-N'-hydroxy-terephthalamide
23. 4-(4-benzyl-piperidine-1-carbonyl)-N-hydroxy-benzamide
24. N-hydroxy-N'-[2-(1-methyl-pyrrolidin-2-yl)-ethyl]-terephthalamide
25. N-(2-ethoxy-benzyl)-N'-hydroxy-terephthalamide
26. N-(2-cyclohex-1-enyl-ethyl)-N'-hydroxy-terephthalamide
27. N-hydroxy-N'-(2-morpholin-4-yl-ethyl)-terephthalamide
28. N-hydroxy-N'-(2-methylsulfanyl-ethyl)-terephthalamide
29. N-hydroxy-N'-(tetrahydro-furan-2-ylmethyl)-terephthalamide

EXAMPLE 17

Evaluation of effects on a human colon carninoma cell line of the compounds of the invention MTT (tetrazolium dye proliferation assay) is widely used for the quantitative determination of cytotoxic effects or in vitro chemosensitivity of tumor cells. The assay is based on the cleavage of the yellow tetrazolium salt MTT to purple formazan crystals by metabolic active cells. For details, see Rubinstein, L. V., et al., J. Natl. Cancer Inst. 82 (1990) 1113–1118.

The following procedure was performed: HT-29 cells (human colon carcinoma cell line) were cultivated in RPMI 1640, 2.5% FCS, 2 mM Glutamine, 100 u/ml Penicillin, 100 ug/ml Streptomycin. For the assay the cells were seeded in 384 well plates, 900 cells per well, in the same medium The next day compounds (dissolved 10 mM in DMSO) were added in various concentrations ranging from 30 uM to 1.5 nM. After 5 days the MTT assay was done mainly according to the instructions of the manufacturer (Cell proliferation kit I, MTT, form Roche Molecular Biochemicals). In brief: MTT labeling reagent was added to a final concentration of 0.5 mg/ml, added and incubated for 4 hrs at 37 C., 5% CO2. During this incubation time purple formazan crystals are formed. After addition of the solubilization solution (20% SDS in 0.02 M HCl) the plates were incubated overnight at 37 C, 5% CO2. After careful mixing plates were measured in Victor 2 (scanning multiwell spectrophotometer, Wallac) at 550 nm.

A decrease in number of living cells results in a decrease in the total metabolic activity in the sample. The decrease directly correlates to the amount of purple colour resulting from the solubilization of the purple formazan crystals. Determination of IC50 was done using XL-fit. The results of this experiment are provided below in Table 1.

TABLE 1

| Compounds according to this invention | IC50 HT29 [$\mu$M] |
|---|---|
| Example 15, No. 128 | 0.02 |
| Example 15, No. 81 | 0.03 |
| Example 15, No. 104 | 0.04 |
| Example 5 | 0.05 |
| Example 15, No. 93 | 0.05 |
| Example 15, No. 94 | 0.07 |
| Example 15, No. 98 | 0.07 |
| Example 2 | 0.11 |
| Example 4 | 0.14 |
| Example 15, No. 90 | 0.14 |
| Example 15, No. 139 | 0.17 |

EXAMPLE 18

Tablet formulation

| Item | Ingredients | mg/Tablet | |
|---|---|---|---|
| 1 | Compound 2a | 25 | 100 |
| 2 | Anhydrous Lactose | 73 | 35 |
| 3 | Croscarmellose Sodium | 6 | 8 |
| 4 | Povidone K30 | 5 | 6 |
| 5 | Magnesium Stearate | 1 | 1 |
| | Total Weight | 110 | 150 |

Compound 2a is described in Example 2.

Procedure:

1. Mix Items 1, 2 and 3 in a suitable mixer for 15 minutes.
2. Granulate the powder mix from Step 1 with 20% Povidone K30 Solution (Item 4).
3. Dry the granulation from Step 2 at 50° C.
4. Pass the granulation from Step 3 through a suitable milling equipment.
5. Add the Item 5 to the milled granulation Step 4 and mix for 3 minutes.
6. Compress the granulation from Step 5 on a suitable press.

List of References

Cancer: Principles & Practice of Oncology, Vincent T. DeVita, Jr., Samuel Hellmann, Steven A. Rosenberg; 5th Ed., Lippincott-Raven Publishers 1997

Houben-Weyl, "Methoden der Organischen Chemie, Georg Thieme Verlag", Stuttgart; Organic Reactions, John Wiley & Sons, Inc., New York Houben-Weyl, Methoden der organischen Chemie, Vol. XV/1 and XV/2

Koyama, Y., et al., Blood 96 (2000) 1490–1495

Marks, P. M., et al., J. Natl. Cancer Inst. 92 (2000) 1210–1216

Org. Prep. and Proced. Int. 3 (6) (1971) 295

Rubinstein, L. V., et al., J. Natl. Cancer Inst. 82 (1990) 1113–1118

U.S. Pat. No. 2,680,731

U.S. Pat. No. 5,369,108

WO 98/55449

Z. Phys. Chem. (Leipzig) 262 (3) (1981) 445–448

What is claimed is:

1. A compound of formula I

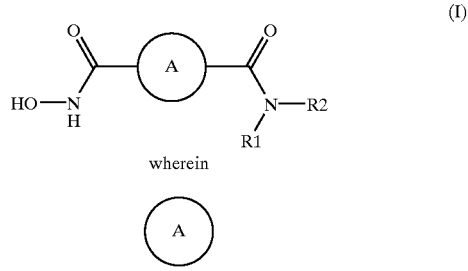

wherein

A is a thiophene ring that may be unsubstituted or substituted by 1 or 2 substituents independently selected from a halogen atom, a $C_{1-4}$-alkyl-, trifluoromethyl-, hydroxy-, $C_{1-4}$-alkoxy-, nitro-, amino-, $C_{1-4}$-alkylamino-, di[$C_{1-4}$-alkyl]-amino-, $C_{1-4}$-alkanoylamino, $C_{1-3}$-alkylenedioxy- or an acyl group; and R1 and R2 are each independently selected from hydrogen, a branched or unbranched $C_{1-4}$-alkyl group that may be unsubstituted or substituted with 1 or more substituents independently selected from halogen, hydroxy-, nitro-, an amino group, a carbocyclic group or a heterocyclic group, and wherein at a chain length of longer than 2 carbon atoms, one or more non adjacent atoms may be replaced by oxygen, nitrogen or sulfur atoms, and wherein 2 atoms may be bound together by a double or triple bond, a carbocyclic group, and a heterocyclic group, or alternatively, the group —$NR^1R^2$ forms a 3–6 membered ring that may contain additional heteroatoms independently selected from nitrogen, oxygen and sulfur, said ring optionally being annulated to a carbocyclic ring or a heterocyclic ring, and said —$NR^1R^2$ ring being unsubstituted or optionally substituted by 1, 2, or 3 substituents independently selected from a halogen atom, an $C_{1-4}$-alkyl-, trifluoromethyl-, hydroxy-, $C_{1-4}$-alkoxy-, aryl-, hetaryl-, arylalkyl, arylalkyloxy-, aryloxy-, $C_{1-3}$-alkylenedioxy-, nitro-, amino-, $C_{1-4}$-alkylamino-, di[$C_{1-4}$-alkyl]amino-, $C_{1-4}$-alkanoylamino- or an acyl-group; and their enantiomers, diastereoisomers, racemates and physiologically acceptable salts thereof.

2. The compound of claim 1 wherein R1 is hydrogen.

3. The compound of claim 1 wherein $R^2$ is benzyl or substituted benzyl.

4. The compound of claim 3 wherein $R^2$ is benzyl or substituted benzyl.

5. The compound of claim 3 wherein $R^2$ is $C_1$–$C_{14}$ alkyl.

6. The compound of claim 1 wherein

is thiophene and the group —$NR^1R^2$ forms a piperazine or piperidine ring that is unsubstituted or is substituted by acetyl, benzhydryl or phenyl wherein the phenyl groups may be substituted by $C_{1-4}$-alkyl, trifluoromethyl-, hydroxy, $C_{1-4}$-alkoxy-, arylalkyloxy-, aryloxy, $C_{1-3}$-alxylenedioxy-, nitro-, amino-, $C_{1-4}$-alkylamino-, di[($C_{1-4}$)alkyl]amino-, $C_{1-4}$-alkanoylamino-, carboxyl-, carboxyalkyl- or an acyl-group.

7. A compound selected from the group consisting of

Thiophene-2,5-dicarboxylic acid 2-hydroxyamide 5-[(naphthalen-1-ylmethyl)-amide];

Thiophene-2,5-dicarboxylic acid 2-hydroxyamide 5-(4-trifluoromethyl-benzylamide);

Thiophene-2,5-dicarboxylic acid 2-(3-chloro-benzylamide) 5-hydroxyamide;

Thiophene-2,5-dicarboxylic acid 2-(3,5-dimethyl-benzylamide) 5-hydroxyamide; and Thiophene-2,5-dicarboxylic acid 2-hexylamide 5-hydroxyamide.

8. A compound selected from the group consisting of

Thiophene-2,4-dicarboxylic acid 2-(3,5-dimethyl-benzylamide) 4-hydroxyamide;

Thiophene-2,4-dicarboxylic acid 2-(3-chloro-benzylamide) 4-hydroxyamide;

Thiophene-2,4-dicarboxylic acid 4-hydroxyamide 2-(4-trifluoromethyl-benzylamide); and Thiophene-2,4-dicarboxylic acid 2-[(benzo[1,3]dioxol-5-ylmethyl)-amide] 4-hydroxyamide.

9. A compound selected from the group consisting of

Thiophene-2,4-dicarboxylic acid 2-hexylamide 4-hydroxyamide;

Thiophene-2,4-dicarboxylic acid 4-(3,5-dimethyl-benzylamide) 2-hydroxyamide;

Thiophene-2,4-dicarboxylic acid 4-(3-chloro-benzylamide) 2-hydroxyamide;

Thiophene-2,4-dicarboxylic acid 4-hexylamide 2-hydroxyamide;

4-{[(5-Hydroxycarbamoyl-thiophene-2-carbonyl)-amino]-methyl}-benzoic acid methyl ester;

5-(4-benzhydryl-piperazine-1-carbonyl)-thiophene-2-carboxylic acid hydroxyamide;

Thiophene-2,5-dicarboxylic acid 2-benzylamide 5-hydroxyamide;

Thiophene-2,5-dicarboxylic acid 2-hydroxyamide 5-[(3-methyl-butyl)-amide];

Thiophene-2,5-dicarboxylic acid 2-hydroxyamide 5-(phenethyl-amide); and

Thiophene-2,5-dicarboxylic acid 2-hydroxyamide 5-{[2-(4-methoxy-phenyl)-ethyl]-amide}.

10. A compound selected from the group consisting of

Thiophene-2,5-dicarboxylic acid 2-(4-fluoro-benzylamide) 5-hydroxyamide;

Thiophene-2,5-dicarboxylic acid 2-hydroxyamide 5-[(1,2,3,4-tetrahydro-naphthalen-1-yl)-amide];

Thiophene-2,5-dicarboxylic acid 2-(2-ethoxy-benzylamide) 5-hydroxyamide;

Thiophene-2,5-dicarboxylic acid 2-(2,4-difluoro-benzylamide) 5-hydroxyamide;

Thiophene-2,5-dicarboxylic acid 2-hydroxyamide 5-indan-1-ylamide;

Thiophene-2,5-dicarboxylic acid 2-[(benzo[1,3]dioxol-5-ylmethyl)-amide] 5-hydroxyamide;

5-(4-phenyl-piperazine-1-carbonyl)-thiophene-2-carboxylic acid hydroxyamide;

Thiophene-2,5-dicarboxylic acid 2-hydroxyamide 5-[(3-isopropoxy-propyl)-amide];

5-(4-acetyl-piperazine-1-carbonyl)-thiophene-2-carboxylic acid hydroxyamide; and Thiophene-2,5-dicarboxylic acid 2-dibutylamide 5-hydroxyamide.

11. A compound selected from the group consisting of 5-(4-benzyl-piperidine-1-carbonyl)-thiophene-2-carboxylic acid hydroxyamide;

Thiophene-2,5-dicarboxylic acid 2-hydroxyamide 5-[(pyridin-3-ylmethyl)-amide];

Thiophene-2,5-dicarboxylic acid 2-cyclohexylamide 5-hydroxyamide;

Thiophene-2,5-dicarboxylic acid 2-cyclopropylamide 5-hydroxyamide;

Thiophene-2,5-dicarboxylic acid 2-hydroxyamide 5-{[2-(1-methyl-pyrrolidin-2-yl)-ethyl]-amide};

Thiophene-2,5-dicarboxylic acid 2-hydroxyamide 5-(2-methoxy-benzylamide);

Thiophene-2,5-dicarboxylic acid 2-[(2-cyclohex-1-enyl-ethyl)-amide] 5-hydroxyamide;

Thiophene-2,5-dicarboxylic acid 2-hydroxyamide 5-[(2-morpholin-4-yl-ethyl)-amide];

Thiophene-2,5-dicarboxylic acid 2-hydroxyamide 5-[(2-methylsulfanyl-ethyl)-amide];

Thiophene-2,5-dicarboxylic acid 2-hydroxyamide 5-[(tetrahydro-furan-2-ylmethyl)-amide];

Thiophene-2,5-dicarboxylic acid 2-hydroxyamide 5-phenylamide; and 5-(morpholine-4-carbonyl)-thiophene-2-carboxylic acid hydroxyamide.

12. A compound selected from the group consisting of

Thiophene-2,5-dicarboxylic acid 2-hydroxyamide 5-[(4-methoxy-phenyl)-amide];

5-(pyrrolidine-1-carbonyl)-thiophene-2-carboxylic acid hydroxyamide;

Thiophene-2,5-dicarboxylic acid 2-[(4-benzyloxy-phenyl)-amide] 5-hydroxyamide;

Thiophene-2,5-dicarboxylic acid 2-[(4-chloro-phenyl)-amide] 5-hydroxyamide;

Thiophene-2,5-dicarboxylic acid 2-hydroxyamide 5-[(4-iodo-phenyl)-amide];

Thiophene-2,5-dicarboxylic acid 2-[(3-ethyl-phenyl)-amide] 5-hydroxyamide;

Thiophene-2,5-dicarboxylic acid 2-[(4-ethyl-phenyl)-amide] 5-hydroxyamide;

Thiophene-2,5-dicarboxylic acid 2-[(3-chloro-phenyl)-amide] 5-hydroxyamide;

Thiophene-2,5-dicarboxylic acid 2-hydroxyamide 5-[(3-iodo-phenyl)-amide]; and 5-(1,4-dioxa-8-aza-spiro[4.5]decane-8-carbonyl)-thiophene-2-carboxylic acid hydroxyamide.

13. A compound selected from the group consisting of

Thiophene-2,5-dicarboxylic acid 2-hydroxyamide 5-(3-morpholin-4-yl-propyl)-amide];

Thiophene-2,5-dicarboxylic acid 2-hydroxyamide 5-pentylamide;

Thiophene-2,5-dicarboxylic acid 2-[(2-diethylamino-ethyl)-amide] 5-hydroxyamide;
Thiophene-2,5-dicarboxylic acid 2-heptylamide 5-hydroxyamide;
Thiophene-2,5-dicarboxylic acid 2-hydroxyamide 5-(isobutyl-amide);
Thiophene-2,5-dicarboxylic acid 2-hydroxyamide 5-nonylamide;
Thiophene-2,5-dicarboxylic acid 2-hydroxyamide 5-[(1-phenyl-ethyl)-amide];
Thiophene-2,5-dicarboxylic acid 2-[2-(4-fluoro-phenyl)-ethyl]-amide 5-hydroxyamide;
Thiophene-2,5-dicarboxylic acid 2-hydroxyamide 5-[2-(5-nitro-pyridin-2-ylamino)-ethyl]-amide; and
Thiophene-2,5-dicarboxylic acid 2-hydroxyamide 5-(3-methyl-benzylamide).

14. A compound selected from the group consisting of
Thiophene-2,5-dicarboxylic acid 2-hydroxyamide 5-[(2-p-tolyl-ethyl)-amide];
Thiophene-2,5-dicarboxylic acid 2-hydroxyamide 5-[3-(2-oxo-pyrrolidin-1-yl)-propyl]-amide;
Thiophene-2,5-dicarboxylic acid 2-hydroxyamide 5-[(2-piperidin-1-yl-ethyl)-amide];
Thiophene-2,5-dicarboxylic acid 2-cyclobutylamide 5-hydroxyamide;
Thiophene-2,5-dicarboxylic acid 2-(2-fluoro-benzylamide) 5-hydroxyamide;
Thiophene-2,5-dicarboxylic acid 2-hydroxyamide 5-[(2-phenyl-propyl)-amide];
Thiophene-2,5-dicarboxylic acid 2-(2,3-dimethoxy-benzylamide) 5-hydroxyamide;
Thiophene-2,5-dicarboxylic acid 2-[(1-benzyl-piperidin-4-yl)-amide] 5-hydroxyamide;
4-[(5-hydroxycarbamoyl-thiophene-2-carbonyl)-amino]-piperidine-1-carboxylic acid ethyl ester; and
Thiophene-2,5-dicarboxylic acid 2-[(3-dimethylamino-2,2-dimethyl-propyl)-amide] 5-hydroxyamide.

15. A compound selected from the group consisting of
Thiophene-2,5-dicarboxylic acid 2-[(3-ethoxy-propyl)-amide] 5-hydroxyamide;
Thiophene-2,5-dicarboxylic acid 2-[(3-dimethylamino-propyl)-amide] 5–58;
Thiophene-2,5-dicarboxylic acid 2-[2-(2-chloro-phenyl)-ethyl]-amide 5-hydroxyamide;
Thiophene-2,5-dicarboxylic acid 2-hydroxyamide 5-(2-trifluoromethyl-benzylamide);
Thiophene-2,5-dicarboxylic acid 2-hydroxyamide 5-(3-trifluoromethyl-benzylamide);
Thiophene-2,5-dicarboxylic acid 2-(2,5-difluoro-benzylamide) 5-hydroxyamide;
Thiophene-2,5-dicarboxylic acid 2-(2,6-difluoro-benzylamide) 5-hydroxyamide;
Thiophene-2,5-dicarboxylic acid 2-(3,4-difluoro-benzylamide) 5-hydroxyamide;
Thiophene-2,5-dicarboxylic acid 2-hydroxyamide 5-[(3-imidazol-1-yl-propyl)-amide]; and
Thiophene-2,5-dicarboxylic acid 2-[(1-cyclohexyl-ethyl)-amide] 5-hydroxyamide.

16. A compound selected from the group consisting of
Thiophene-2,5-dicarboxylic acid 2-[2-(3-chloro-phenyl)-ethyl]-amide 5-hydroxyamide;
Thiophene-2,5-dicarboxylic acid 2-[2-(3-fluoro-phenyl)-ethyl]-amide 5-hydroxyamide;
Thiophene-2,5-dicarboxylic acid 2-[2-(2,4-dichloro-phenyl)-ethyl]-amide 5-hydroxyamide;
Thiophene-2,5-dicarboxylic acid 2-cyclopropylmethyl-amide 5-hydroxyamide;
Thiophene-2,5-dicarboxylic acid 2-[2-(2-fluoro-phenyl)-ethyl]-amide 5-hydroxyamide;
Thiophene-2,5-dicarboxylic acid 2-[(4-diethylamino-1-methyl-butyl)-amide] 5-hydroxyamide;
Thiophene-2,5-dicarboxylic acid 2-hydroxyamide 5-[(2-pyridin-2-yl-ethyl)-amide];
Thiophene-2,5-dicarboxylic acid 2-hydroxyamide 5-[(2-pyrrolidin-1-yl-ethyl)-amide];
Thiophene-2,5-dicarboxylic acid 2-hydroxyamide 5-[(1-methyl-hexyl)-amide]; and
Thiophene-2,5-dicarboxylic acid 2-cycloheptylamide 5-hydroxyamide.

17. A compound selected from the group consisting of
Thiophene-2,5-dicarboxylic acid 2-cyclopentylamide 5-hydroxyamide;
Thiophene-2,5-dicarboxylic acid 2-(2,4-dichloro-benzylamide) 5-hydroxyamide;
Thiophene-2,5-dicarboxylic acid 2-[(3-diethylamino-propyl)-amide] 5-hydroxyamide;
Thiophene-2,5-dicarboxylic acid 2-[(1,5-dimethyl-hexyl)-amide] 5-hydroxyamide;
Thiophene-2,5-dicarboxylic acid 2-[(2,2-diphenyl-ethyl)-amide] 5-hydroxyamide;
3-[(5-hydroxycarbamoyl-thiophene-2-carbonyl)-amino]-butyric acid ethyl ester;
Thiophene-2,5-dicarboxylic acid 2-[(2-ethyl-hexyl)-amide] 5-hydroxyamide;
Thiophene-2,5-dicarboxylic acid 2-hydroxyamide 5-(4-methoxy-benzylamide);
Thiophene-2,5-dicarboxylic acid 2-hydroxyamide 5-(4-methyl-benzylamide); and
Thiophene-2,5-dicarboxylic acid 2-hydroxyamide 5-[(3-phenyl-propyl)-amide].

18. A compound selected from the group consisting of
Thiophene-2,5-dicarboxylic acid 2-[(2-diisopropylamino-ethyl)-amide] 5-hydroxyamide;
Thiophene-2,5-dicarboxylic acid 2-hydroxyamide 5-[2-(4-nitro-phenyl)-ethyl]-amide;
Thiophene-2,5-dicarboxylic acid 2-[(3,3-diphenyl-propyl)-amide] 5-hydroxyamide;
Thiophene-2,5-dicarboxylic acid 2-(2-amino-benzylamide) 5-hydroxyamide;
Thiophene-2,5-dicarboxylic acid 2-(4-bromo-benzylamide) 5-hydroxyamide;
Thiophene-2,5-dicarboxylic acid 2-(3,5-bis-trifluoromethyl-benzylamide) 5-hydroxyamide;
Thiophene-2,5-dicarboxylic acid 2-(3-bromo-benzylamide) 5-hydroxyamide;
Thiophene-2,5-dicarboxylic acid 2-(3-fluoro-benzylamide) 5-hydroxyamide;
Thiophene-2,5-dicarboxylic acid 2-hydroxyamide 5-(3-methoxy-benzylamide); and
Thiophene-2,5-dicarboxylic acid 2-(2-chloro-6-fluoro-benzylamide) 5-hydroxyamide.

19. A compound selected from the group consisting of
Thiophene-2,5-dicarboxylic acid 2-(4-tert-butyl-benzylamide) 5-hydroxyamide;
Thiophene-2,5-dicarboxylic acid 2-hydroxyamide 5-{[2-(4-sulfamoyl-phenyl)-ethyl]-amide};

Thiophene-2,5-dicarboxylic acid 2-[(2-benzylsulfanyl-ethyl)-amide] 5-hydroxyamide;
Thiophene-2,5-dicarboxylic acid 2-hydroxyamide 5-{[2-(4-hydroxy-phenyl)-ethyl]-amide};
Thiophene-2,5-dicarboxylic acid 2-{[2-(4-chloro-phenyl)-ethyl]-amide} 5-hydroxyamide;
Thiophene-2,5-dicarboxylic acid 2-{[2-(3,4-dimethoxy-phenyl)-ethyl]-amide} 5-hydroxyamide;
Thiophene-2,5-dicarboxylic acid 2-hydroxyamide 5-[(2-phenoxy-ethyl)-amide];
Thiophene-2,5-dicarboxylic acid 2-hydroxyamide 5-[(4-phenyl-butyl)-amide];
Thiophene-2,5-dicarboxylic acid 2-[(3,4-dimethyl-phenyl)-amide] 5-hydroxyamide; and
5-(4-Pyrimidin-2-yl-piperazine-1-carbonyl)-thiophene-2-carboxylic acid hydroxyamide.

20. A compound selected from the group consisting of
Thiophene-2,5-dicarboxylic acid 2-[(3,4-dimethoxy-phenyl)-amide] 5-hydroxyamide;
Thiophene-2,5-dicarboxylic acid 2-[(4-tert-butyl-phenyl)-amide] 5-hydroxyamide;
Thiophene-2,5-dicarboxylic acid 2-hydroxyamide 5-[(4-methoxy-2-methyl-phenyl)-amide];
Thiophene-2,5-dicarboxylic acid 2-[(4-dimethylamino-phenyl)-amide] 5-hydroxyamide;
Thiophene-2,5-dicarboxylic acid 2-hydroxyamide 5-[(4-phenoxy-phenyl)-amide];
Thiophene-2,5-dicarboxylic acid 2-hydroxyamide 5-p-tolylamide;
Thiophene-2,5-dicarboxylic acid 2-hydroxyamide 5-[(4-piperidin-1-yl-phenyl)-amide];
1-(5-Hydroxycarbamoyl-thiophene-2-carbonyl)-piperidine-4-carboxylic acid methyl ester;
Thiophene-2,5-dicarboxylic acid 2-hydroxyamide 5-[methyl-(1-methyl-piperidin-4-yl)-amide]; and
Thiophene-2,5-dicarboxylic acid 2-hydroxyamide 5-{methyl-[2-(4-nitro-phenyl)-ethyl]-amide}.

21. A compound selected from the group consisting of
Thiophene-2,5-dicarboxylic acid 2-(butyl-methyl-amide) 5-hydroxyamide;
Thiophene-2,5-dicarboxylic acid 2-diethylamide 5-hydroxyamide;
Thiophene-2,5-dicarboxylic acid 2-[(4-cyclohexyl-phenyl)-amide] 5-hydroxyamide;
Thiophene-2,5-dicarboxylic acid 2-hydroxyamide 5-[methyl-(2-methylamino-ethyl)-amide];
Thiophene-2,5-dicarboxylic acid 2-[ethyl-(3-ethylamino-propyl)-amide] 5-hydroxyamide;
5-[4-(2-Morpholin-4-yl-2-oxo-ethyl)-piperazine-1-carbonyl]-thiophene-2-carboxylic acid hydroxyamide;
5-(4-Dimethylcarbamoylmethyl-piperazine-1-carbonyl)-thiophene-2-carboxylic acid hydroxyamide;
5-[4-(2-Oxo-2-piperidin-1-yl-ethyl)-piperazine-1-carbonyl]-thiophene-2-carboxylic acid hydroxyamide;
Thiophene-2,5-dicarboxylic acid 2-hydroxyamide 5-(3-trifluoromethoxy-benzylamide); and
Thiophene-2,5-dicarboxylic acid 2-hydroxyamide 5-(3-phenoxy-benzylamide).

22. A compound selected from the group consisting of
Thiophene-2,5-dicarboxylic acid 2-hydroxyamide 5-[(1-methyl-3-phenyl-propyl)-amide];
Thiophene-2,5-dicarboxylic acid 2-hydroxyamide 5-[(3-methoxy-propyl)-amide];
Thiophene-2,5-dicarboxylic acid 2-(4-chloro-benzylamide) 5-hydroxyamide;
Thiophene-2,5-dicarboxylic acid 2-[(2-acetylamino-ethyl)-amide] 5-hydroxyamide;
Thiophene-2,5-dicarboxylic acid 2-hydroxyamide 5-[(1-methyl-heptyl)-amide];
Thiophene-2,5-dicarboxylic acid 2-hydroxyamide 5-[(1-methyl-butyl)-amide];
Thiophene-2,5-dicarboxylic acid 2-allylamide 5-hydroxyamide;
Thiophene-2,5-dicarboxylic acid 2-[(1,3-dimethyl-butyl)-amide] 5-hydroxyamide;
Thiophene-2,5-dicarboxylic acid 2-hydroxyamide 5-propylamide;
Thiophene-2,5-dicarboxylic acid 2-sec-butylamide 5-hydroxyamide;
Thiophene-2,5-dicarboxylic acid 2-butylamide 5-hydroxyamide;
Thiophene-2,5-dicarboxylic acid 2-(3,4-dichloro-benzylamide) 5-hydroxyamide; and
Thiophene-2,5-dicarboxylic acid 2-(2,3-dichloro-benzylamide) 5-hydroxyamide.

23. A process of manufacturing a compound of formula I comprising
reacting a compound of formula III

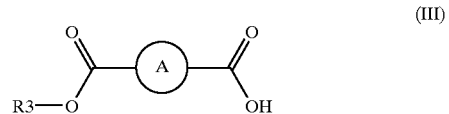

(III)

with an amine of the formula HNR$_1$R$_2$ in the presence of an activating agent, to give a compound of formula II

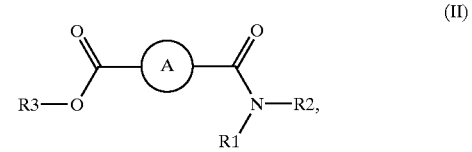

(II)

and
reacting the compound of formula II with hydroxylamine in the presence of a suitable base,
wherein

is a thiophene ring that may be unsubstituted or substituted by 1 or 2 substituents independently selected from a halogen atom, a $C_{1-4}$-alkyl-, trifluoromethyl-, hydroxy-, $C_{1-4}$-alkoxy-, nitro-, amino-, $C_{1-4}$-alkylamino-, di[$C_{1-4}$-alkyl]-amino-, $C_{1-4}$-alkanoylamino, $C_{1-3}$-alkylenedioxy- or an acyl group; and R1 and R2 are each independently selected from
hydrogen,
a branched or unbranched $C_{1-14}$-alkyl group that may be unsubstituted or substituted with 1 or more substituents independently selected from halogen, hydroxy-, nitro-, an amino group, a carbocyclic group or a heterocyclic group, and wherein at a chain length of longer than 2 carbon atoms, one or more non adjacent atoms may be replaced by oxygen, nitrogen or sulfur atoms, and wherein 2 atoms may be bound together by a double or triple bond, a carbocyclic group, and a heterocyclic group, or alternatively, the group —NR$^1$R$^2$ forms a 3–6 membered ring that may contain additional heteroatoms independently selected from nitrogen, oxygen and sulfur, said ring optionally being annulated to a carbocyclic ring or a heterocyclic ring, and said —NR$^1$R$^2$ ring being unsubstituted or optionally substituted by 1, 2, or 3 substituents independently selected from a halogen atom, an $C_{1-4}$-alkyl-, trifluoromethyl-, hydroxy-, $C_{1-4}$-alkoxy-, aryl-, hetaryl-, arylalkyl, arylalkyloxy-, aryloxy, $C_{1-3}$-alkylenedioxy-, nitro-, amino-, $C_{1-4}$-alkylamino-, di[$C_{1-4}$-alkyl]amino-, $C_{1-4}$-alkanoylamino- or an acyl-group; and R3 is $C_{1-4}$-alkyl.

24. A pharmaceutical composition comprising a therapeutically effective amount of a compound of claim 1, and a pharmaceutically acceptable carrier or excipient.

25. A method of treating breast, lung, colon, rectal, stomach, prostate, bladder, pancreas or ovarian cancer comprising administering to a subject in need of such treatment a therapeutically effective amount of a compound of claim 1.

26. A compound of formula

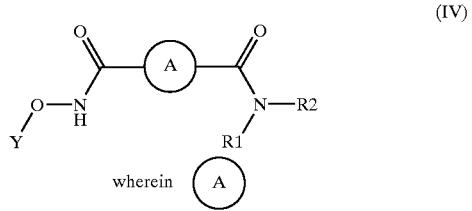

(IV)

wherein A is a thiophene ring that may be unsubstituted or substituted by 1 or 2 substituents independently selected from a halogen atom, a $C_{1-4}$-alkyl-, trifluoromethyl-, hydroxy-, $C_{1-4}$-alkoxy-, nitro-, amino-, $C_{1-4}$-alkylamino-, di[$C_{1-4}$-alkyl]-amino-, $C_{1-4}$-alkanoylamino, $C_{1-3}$-alkylenedioxy- or an acyl group; and R1 and R2 are each independently selected from hydrogen, a branched or unbranched $C_{1-14}$-alkyl group that may be unsubstituted or substituted with 1 or more substituents independently selected from halogen, hydroxy-, nitro-, an amino group, a carbocyclic group or a heterocyclic group, and wherein at a chain length of longer than 2 carbon atoms, one or more non adjacent atoms may be replaced by oxygen, nitrogen or sulfur atoms, and wherein 2 atoms may be bound together by a double or triple bond, a carbocyclic group, and a heterocyclic group, or alternatively, the group —NR$^1$R$^2$, forms a 3–6 membered ring that may contain additional heteroatoms independently selected from nitrogen, oxygen and sulfur, said ring optionally being annulated to a carbocyclic ring or a heterocyclic ring, and said —NR$^1$R$^2$ ring being unsubstituted or optionally substituted by 1, 2, or 3 substituents independently selected from a halogen atom, an $C_{1-4}$-alkyl-, trifluoromethyl-, hydroxy-, $C_{1-4}$-alkoxy-, aryl-, hetaryl-, arylalkyl, arylalkyloxy-, aryloxy, $C_{1-3}$-alkylenedioxy-, nitro-, amino-, $C_{1-4}$-alkylamino-, di[$C_{1-4}$-alkyl]amino-, $C_{1-4}$-alkanoylamino- or an acyl-group; and Y is a protecting group.

27. A compound selected from the group consisting of thiophene-2,5-dicarboxylic acid 2-(2,3-difluoro-benzylamide) 5-hydroxyamide;

thiophene-2,5-dicarboxylic acid 2-(2-chloro-benzylamide) 5-hydroxyamide;

thiophene-2,5-dicarboxylic acid 2-(3,4-dimethoxy-benzylamide) 5-hydroxyamide;

thiophene-2,5-dicarboxylic acid 2-(3,5-difluoro-benzylamide) 5-hydroxyamide;

thiophene-2,5-dicarboxylic acid 2-[(2-amino-phenyl)-amide] 5-hydroxyamide;

thiophene-2,5-dicarboxylic acid 2-[4-(2-amino-phenylcarbamoyl)-benzylamide] 5-(benzyloxy-amide); and thiophene-2,5-dicarboxylic acid 2-hydroxyamide 5-[methyl-(4-trifluoromethyl-benzyl)-amide].

* * * * *

UNITED STATES PATENT AND TRADEMARK OFFICE
CERTIFICATE OF CORRECTION

PATENT NO.    : 6,784,173 B2
DATED         : August 31, 2004
INVENTOR(S)   : Ulrike Leser-Reiff, Tim Sattelkau and Gerd Zimmermann It is certified that error appears in the above-identified patent and that said Letters Patent is hereby corrected as shown below:

Column 20,
Line 37, "a branched or unbranched $C_{1-4}$-alkyl group" should read -- a branched or unbranched $C_{1-14}$-alkyl group --.

Column 21,
Line 13, "$C_{1-3}$-alxylenedioxy-," should read -- $C_{1-3}$-alkylenedioxy-, --.

Signed and Sealed this

Twenty-first Day of December, 2004

JON W. DUDAS
*Director of the United States Patent and Trademark Office*